United States Patent
Taylor

(10) Patent No.: US 6,426,056 B2
(45) Date of Patent: *Jul. 30, 2002

(54) APPARATUS AND METHOD FOR PREPARATION OF A PERITONEAL DIALYSIS SOLUTION

(75) Inventor: Michael A. Taylor, Napa, CA (US)

(73) Assignee: PRISMedical Corporation, Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/908,785

(22) Filed: Jul. 18, 2001

Related U.S. Application Data

(63) Continuation of application No. 09/277,448, filed on Mar. 26, 1999, now Pat. No. 6,274,103.

(51) Int. Cl.[7] ............................................... B01D 11/02
(52) U.S. Cl. ..................... 422/261; 210/232; 210/257.1; 210/650; 604/221; 604/416; 422/255
(58) Field of Search ................................. 422/255, 261; 210/650, 232, 257.1; 604/416, 221

(56) References Cited

U.S. PATENT DOCUMENTS

| | | | |
|---|---|---|---|
| 3,730,349 A | * | 5/1973 | Herrmann |
| 4,280,912 A | * | 7/1981 | Berry, III et al. |
| 4,467,588 A | * | 8/1984 | Carveth |
| 4,495,067 A | * | 1/1985 | Klein et al. |
| 4,548,606 A | * | 10/1985 | Larkin |
| 4,756,838 A | * | 7/1988 | Veltman |
| 4,784,495 A | * | 11/1988 | Jonsson et al. |
| 4,871,463 A | * | 10/1989 | Taylor et al. |
| 5,071,558 A | * | 12/1991 | Itob |
| 5,110,479 A | * | 5/1992 | Frommer et al. |
| 5,259,954 A | * | 11/1993 | Taylor |
| 5,344,231 A | * | 9/1994 | Jonsson et al. |
| 5,395,323 A | * | 3/1995 | Berglund |
| 5,511,875 A | * | 4/1996 | Jonsson et al. |
| 5,685,980 A | * | 11/1997 | Patapoff et al. |
| 5,725,777 A | * | 3/1998 | Taylor |

* cited by examiner

Primary Examiner—Krisanne Thornton
(74) Attorney, Agent, or Firm—Knobbe, Martens, Olson & Bear, LLP

(57) ABSTRACT

The invention provides an apparatus and method for storing and transporting peritoneal dialysate in dry or lyophilized form, and for forming a deliverable peritoneal dialysis solution therefrom. In one embodiment, a dry reagent bed, including reagents sufficient to produce a dialysis solution, is suspended in a diluent flow path through the apparatus housing. Continuous pressure on the reagent bed causes the bed to compact as it erodes when purified water is passed through the housing. The pressure ensures complete and even dissolution of the reagents. Through dry storage and simple dissolution, even in a home, the invention enables a wider variety of solution constituents, including reduced acid content and the use of bicarbonate as a stable buffer component. The latter is illustrated in a double-bed embodiment, where bicarbonate is stored separately from calcium or magnesium salts within a single housing.

20 Claims, 7 Drawing Sheets

APPARATUS AND METHOD FOR PREPARATION OF A PERITONEAL DIALYSIS SOLUTION

RELATED APPLICATION

This application is a continuation of U.S. patent application Ser. No. 09/227,448, filed on Mar. 26, 1999 now U.S. Pat. No. 6,274,103.

FIELD OF THE INVENTION

The invention generally relates to peritoneal dialysis, and more particularly to devices and methods for producing a peritoneal dialysis solution from dry reagents.

BACKGROUND OF THE INVENTION

Treatments for patients having substantially impaired renal function, or kidney failure, are known as "dialysis." Either blood dialysis ("hemodialysis") or peritoneal dialysis methods may be employed. Both methods essentially involve the removal of toxins from body fluids by diffusion of the toxins from the body fluids into a toxin free dialysis solution.

Hemodialysis involves removing blood from the patient, circulating the blood through a dialysis machine outside the body, and returning the blood to the patient. As the blood is directly in contact with the hemodialysis membrane, the patient ordinarily needs to be treated only 3–5 hours at a time, about three times per week. Unfortunately, hemodialysis requires the use of complex and expensive equipment, and can therefore normally only be performed under controlled conditions of a hospital or other specialized clinic.

Peritoneal dialysis, on the other hand, can be performed where such complex equipment is not readily available, such as in the patient's home. In the peritoneal dialysis process, the patient's peritoneal cavity is filled with a dialysate solution. Dialysates are formulated with a high concentration of the dextrose, as compared to body fluids, resulting in an osmotic gradient within the peritoneal cavity. The effect of this gradient is to cause body fluids, including impurities, to pass through the peritoneal membrane and mix with the dialysate. By flushing the dialysate from the cavity, the impurities can be removed.

Due to indirect contact with bodily fluids through bodily tissues, rather than direct contact with blood, the dextrose concentration needs to be considerably higher in peritoneal dialysis than in hemodialysis, and the treatment is generally more prolonged. Peritoneal dialysis may be performed intermittently or continuously. In an intermittent peritoneal dialysis (IPD) procedure, the patient commonly receives two liters of dialysate at a time. For example, in a continuous ambulatory peritoneal dialysis (CAPD) procedure, the peritoneal cavity is filled with two liters of dialysate and the patient is the free to move about while diffusion carries toxins into the peritoneal cavity. After about 4–6 hours, the peritoneum is drained of toxified dialysate over the course of an hour. This process is repeated two to three times per day each day of the week. Continuous Cycle Peritoneal Dialysis (CCPD) in contrast, involves continuously feeding and flushing dialysate solution through the peritoneal cavity, typically as the patient sleeps.

Because peritoneal dialysates are administered directly into the patient's body, it is important that the dialysis solution maintains the correct proportions and concentrations of reagents. Moreover, it is impractical to formulate and mix dialysis solutions on site at the typical location of administration, such as the patient's home. Accordingly, peritoneal dialysates are typically delivered to the site of administration in pre-mixed solutions.

Unfortunately, dialysis solutions are not stable in solutions over time. For example, dextrose has a tendency to caramelize in solution over time, particularly in the concentrations required in the peritoneal dialysis context. To prevent such caramelization, peritoneal dialysis solutions are typically acidified, such as with hydrochloric acid, lactate or acetate, to a pH between 4.0 and 6.5. The ideal pH level for a peritoneal dialysate, however, is between 7.2 and 7.4. While achieving the desired goal of stabilizing dextrose in solution, the pH of acidified peritoneal dialysis solutions tends to damage the body's natural membranes after extended periods of dialysis. Additionally, the use of acidified peritoneal dialysates tends to induce acidosis in the patient.

Bicarbonates introduce further instability to dialysis solutions. The most physiologically compatible buffer for a peritoneal dialysate is bicarbonate. Bicarbonate ions react undesirably with other reagents commonly included in dialysate solutions, such as calcium or magnesium in solution, precipitating out of solution as insoluble calcium carbonate or magnesium carbonate. These insolubles can form even when the reactants are in dry form. When occurring in solution, the reactions also alter the pH balance of the solution through the liberation of carbon dioxide ($CO_2$). Even in the absence of calcium or magnesium salts, dissolved sodium bicarbonate can spontaneously decompose into sodium carbonate and $CO_2$, undesirably lowering the solution's pH level.

The current alternatives to bicarbonate for buffering peritoneal dialysate are acetate and lactate, but these reagents also have undesirable chemical consequences. For example, there is some evidence that acetate may reduce osmotic ultrafiltration and may induce fibrosis of the peritoneal membrane.

The incompatibility of reagents commonly found in dialysates thus creates significant logistical problems in connection with their preparation, storage and transportation. Attempted solutions to these problems have included various devices and methods for providing dry formulations of reagents, and for separately storing and dissolving incompatible reagents. See, e.g., U.S. Pat. Nos. 4,467,588, 4,548, 606, 4,756,838, 4,784,495, 5,344,231 and 5,511,875. Many of these proposed systems involve elaborate water pumping and re-circulation systems, pH and conductivity monitors and water heating components. Moreover, sterile water must be provided independently, further complicating the formulation process.

While many prior methods and devices have been successful to one degree or another in addressing logistical problems, they have proven unsatisfactory for various reasons. Conventional systems are quite complex and expensive, such that they are impractical for many settings. Thus, dialysate solutions still tend to be prepared well in advance of administration, risking destabilization and/or requiring acidification of the solutions, as noted above. Additionally, pre-formulated solutions are quite bulky and involve considerable transportation and storage expense.

Accordingly, a need exists for improved methods and devices for formulating solutions for peritoneal dialysis. Desirably, such methods and devices should avoid the problems of non-physiologic solutions and incompatibility of dialysate reagents, and also simplify transportation, storage and mixing of such dialysates.

SUMMARY OF THE INVENTION

In satisfying the aforementioned needs, the present invention provides an apparatus and method for producing dialysis solutions from dry reagents immediately prior to administration. The invention thereby allow production of physiologically compatible dialysate solutions and minimizes the likelihood of undesirable reactions among reagents. Moreover, the invention facilitates separation of incompatible reagents. Both of these features, independently and in combination, result in a relatively simple and inexpensive apparatus for storing, transporting and producing solution from peritoneal dialysis reagents in dry form. Moreover, the devices and methods expand options for practically applicable solution formulations.

In accordance with one aspect of the present invention, for example, an apparatus is provided for producing a peritoneal dialysis solution. The apparatus includes a housing, which defines a fluid flow path through it. At least one reagent bed is kept within the housing along the fluid flow path. The reagent bed includes dry reagents in proportions suitable for peritoneal dialysis.

In accordance with another aspect of the invention, an apparatus produces a complete peritoneal dialysis solution. The apparatus includes a first dry reagent bed and a second dry reagent bed, which is spaced from the first reagent bed. Additionally, the apparatus includes means for compressing the first and second reagent beds.

In accordance with another aspect of the invention, an apparatus is provided for producing a peritoneal dialysis solution from dry reagents. The apparatus includes a housing with a first reagent bed disposed within the housing. The first reagent bed includes a plurality of chemically compatible reagents. A second reagent bed is also disposed within the housing, spaced from the first reagent bed. The second reagent bed includes a reagent that is chemically incompatible with at least one of the plurality of reagents of the first reagent bed. Additionally, a first compression component is disposed within the housing upstream of the first reagent bed, while a second compression component is disposed within the housing between the first and second reagent beds. A third compression component is disposed within the housing downstream of the second reagent bed.

In accordance with still another aspect of the invention, a system is provided for producing a peritoneal dialysis solution. A reagent cartridge houses at least one dry reagent bed and at least one compression component, which exerts continual pressure on the reagent bed. A water purification pack is configured to connect upstream of the reagent cartridge. The water purification pack houses filters, activated carbon and ion exhange resins such as to convert potable water to injectable quality water.

In accordance with still another aspect of the invention, a method is provided for producing a peritoneal dialysis solution. Diluent passes through a dry reagent bed, thereby consuming reagents in the bed. The diluent then carries the consumed reagents out of the bed. The reagent bed is compacted as the reagents are consumed.

In accordance with still another aspect of the invention, a method is disclosed for producing a peritoneal dialysis solution from purified water. Purified water passes into a reagent cartridge housing, which contains dry reagents sufficient to produce a complete peritoneal dialysis solution. The reagents dissolve in the purified water as it passes through the reagent cartridge.

BRIEF DESCRIPTION OF THE DRAWINGS

These and other aspects of the invention will be apparent to the skilled artisan in view of the Detailed Description and claims set forth below, and in view of the appended drawings, which are meant to illustrate and not to limit the invention, and wherein:

DETAILED DESCRIPTION OF THE PREFERRED EMBODIMENT

While the illustrated embodiments are described in the context of particular formulations and relative proportions of reagents, the skilled artisan will find application for the described methods and devices in a variety of different formulations and proportions of reagents.

System for Preparing Peritoneal Dialysis Solution

Figure 1:
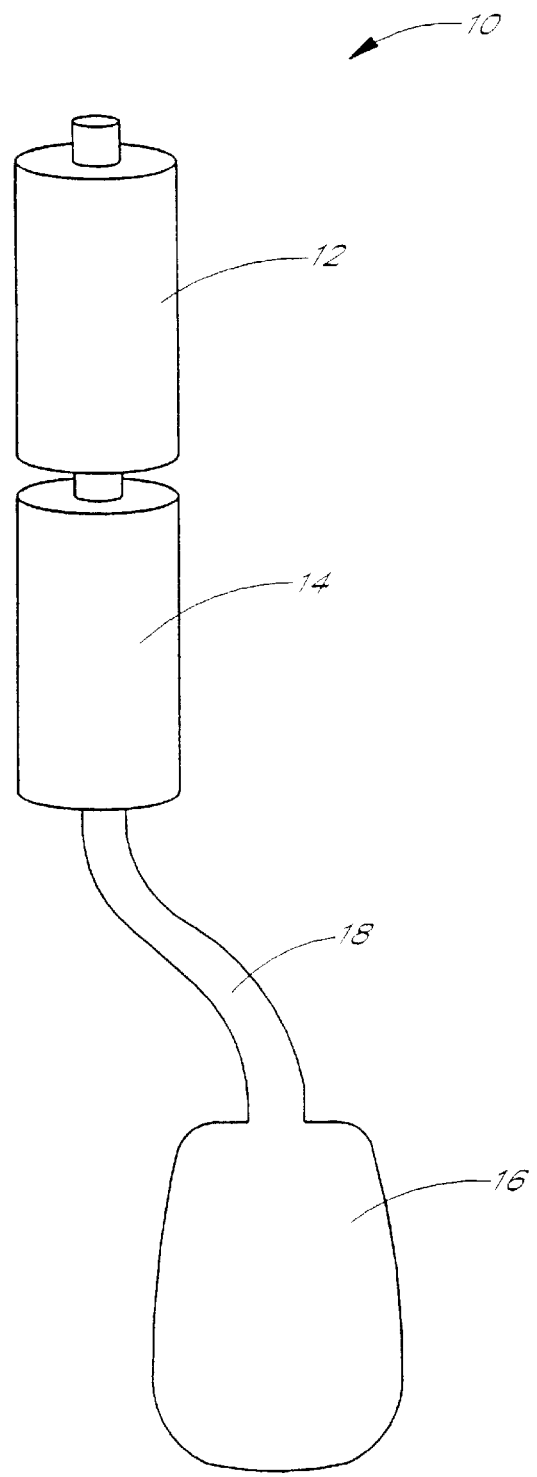
FIG. 1 is a schematic side perspective view of a system for producing peritoneal dialysate, constructed in accordance with one aspect of the present invention.

FIG. 1 illustrates a system 10 for producing solutions suitable for peritoneal dialysis. As illustrated, a purified diluent source 12 is connected upstream of a reagent cartridge 14. The cartridge 14, in turn, is in fluid communication with a dialysate reservoir 16 via a tube 18. As set forth in more detail below, purified diluent is provided from the source 12 to the reagent cartridge 14, wherein the dry reagents are dissolved and peritoneal dialysis solution is delivered to the reservoir 16. Alternatively, the solution can be delivered directly to the peritoneal cavity. Advantageously, the solution can be so formed immediately prior to delivery to the patient's peritoneal cavity, such that the dialysate need not be stored in solution form for extended periods, and little opportunity exists undesirable reactions within the solution prior to delivery.

The cartridge 14 advantageously houses dry or lyophilized formulations of reagents suitable for peritoneal dialysis. The cartridge 14 also defines fluid flow paths through the dry reagents, by way of porous elements therebetween, enabling dry storage in confined reagent beds while also enabling dissolution simply by passing diluent through the housing. Two preferred versions of the cartridge 14 are described in more detail with respect to FIGS. 3–7, below.

In the illustrated embodiment, the diluent source 12 comprises a water purification pack capable of on-site purification of locally available water, such as tap water from a municipal water source. The preferred water purification pack is described in more detail with respect to FIG. 2 below. It will be understood, however, that the skilled artisan will find application for the illustrated reagent cartridge 14 with or without the preferred purification pack. For example, the purified diluent source 12 in other arrangements can comprise a store of pre-sterilized water.

Water Purification Pack

Figure 2:
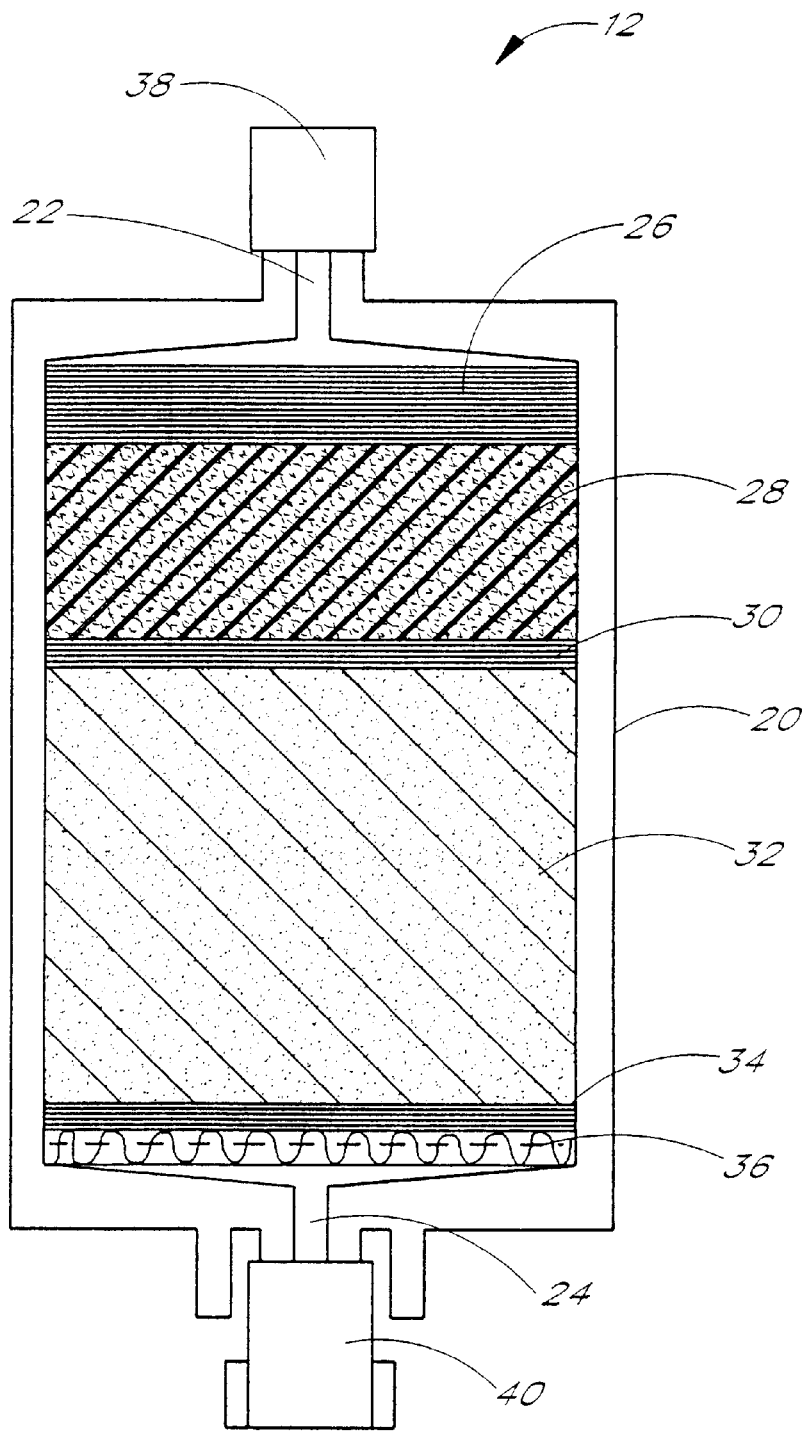
FIG. 2 is a schematic side sectional view of a water purification pack, constructed in accordance with the preferred embodiments.

Referring to FIG. 2, the preferred purified diluent source 12 comprises a fluid purification pack, capable of instantaneously purifying water or other diluent to the standards required for injection into a patient, and particularly for peritoneal dialysis applications. Advantageously, available water (e.g., tap water) can be introduced to the system, water is purified as it travels through the pack, and the purified water is delivered directly to the reagent cartridge 14 (FIG. 1). Accordingly, storage of bulky purified water and complex machinery for purifying water is obviated.

Conventionally, purifying non-sterile water to the quality standards required for use as a diluent for introduction into the human body requires extensive mechanical filtration, pumping, distribution and monitoring systems. These complex mechanisms are eliminated in the preferred embodiment of the present invention by purifying water through the purification pack of FIG. 2. This compact, lightweight pack is capable of purifying water, at the point of administration, in compliance with the water quality standards set forth in the U.S. Pharmacopoeia for "Sterile Water for Injection."

In the illustrated embodiment, the water purification pack 12 comprises a housing 20 with an axial inlet 22 and outlet 24. The housing is preferably formed of a suitable polymer, particularly polycarbonate, which aids in purifying water by binding endotoxins through charge interactions.

Immediately downstream of the housing inlet 22 is a depth filter 26. The depth filter retains insoluble particulates and microbes greater than the pore size of this component. The porosity of the illustrated depth filter 26 is preferably from 1 to 10 microns, most preferably about 1 micron. The depth filter 26 is preferably formed of a porous polypropylene mesh in multiple layers, particularly 2–3 layers in the illustrated embodiment. Alternatively, the commercially available cellulose-based depth filters can be employed, as will be understood by one of ordinary skill in the art.

Downstream of the depth filter 26 is a bed of granular carbon 28. This component removes certain residual organic contaminants, such as endotoxins, as well as commonly used additives placed in the municipally treated waters (e.g., chlorine, trihalomethanes and chloramine).

Adjacent to the downstream end of the granular carbon bed 28 is a carbon bed restraint 30. The restraint 30 is a filter of controlled porosity, preferably also comprising a polypropylene mesh with a porosity of about 1–10 microns, more preferably about 1 micron. This component prevents passage of particulates shed by the granular carbon bed 28, as well as providing a secondary assurance that insoluble particulates do not pass further through the water purification pack.

Adjacent to the downstream side of the carbon bed restraint 30 is a bed 32 of deionization resin beads. The resin bed 32 comprises a mixture of pharmaceutical grade resins with strong anion exchanger and strong cation exchanger chemistries, binding dissociable ions and other charged particles with a very high affinity. Such resins are available, for example, from Rohm & Haas of Philadelphia, Pa. under the trade name IRN 150, or from Sybron of Birmingham, N.J. under the trade name NM60. The resin bed 32 also retains endotoxins which escape the upstream filtration components.

Downstream of the deionization resin bed 32 is a deionization bed restraint 34 and a terminal filter element 36, in sequence. The restraint 34 preferably comprises the same polypropylene mesh utilized for the illustrated depth filter 26 and carbon bed restraint 30. The resin bed restraint 34 serves to prevent passage of deionization bed fragments or fines, as well as any other particulates that have escaped the upstream filters 26, 30. The restraint 34 also serves to protect the filter element 36 downstream of the restraint 34.

The terminal filter element 36 consists of a 0.2 micron or finer micro- to ultra-filtration membrane, chemically treated to incorporate a quaternary amine exchanger to bind endotoxins. Alternatively, the terminal filter can comprise a 0.2 micron or finer filter along with a second membrane having enhanced endotoxin binding characteristics. Such endotoxin binding membranes are available under the trade name HP200 from the Pall Specialty Materials Co. The terminal filter 36 thus removes endotoxins, as well as microbes and particulate matter of less than 1 micron, from water passing therethrough. Desirably, the porosity can be as low as a 10,000 molecular weight cutoff, sufficient to filter many viruses.

Water passing through the pack 12 and exiting the housing outlet 24 conforms to the water quality standards set forth in the U.S. Pharmacopoeia procedures for "Sterile Water for Injection," as noted above.

Desirably, the water purification pack 12 includes an upstream cap 38 over the housing inlet 22, and a downstream cap 40 over the housing outlet 24. The sterility of the purification elements housed within the housing 20 are thus maintained until use. As will be understood in the art, the inlet 12 and outlet 24 can be provided with threads or Luer-type fittings to mate with upstream and downstream elements in the peritoneal dialysate delivery system 10 (FIG. 1).

A similar water purification pack is described at Col. 7, line 19 to Col. 8, line 24 of U.S. Pat. No. 5,725,777, entitled Reagent/Drug Cartridge, the disclosure of which is incorporated herein by reference.

Single-Bed Reagent Cartridge

Figure 3:
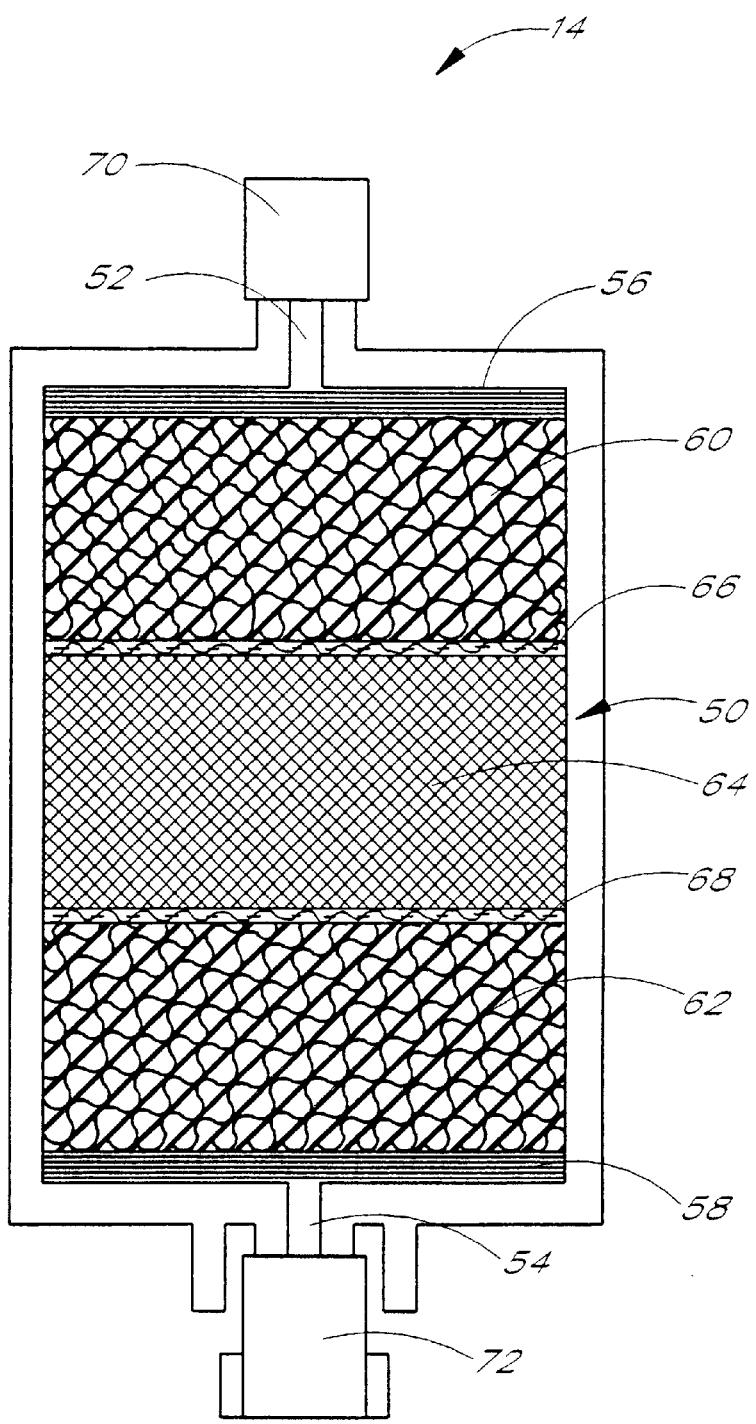
FIG. 3 is a schematic side sectional view of a reagent cartridge for housing reagents of peritoneal dialysate, constructed in accordance with a preferred embodiment of the present invention.
Figure 4:
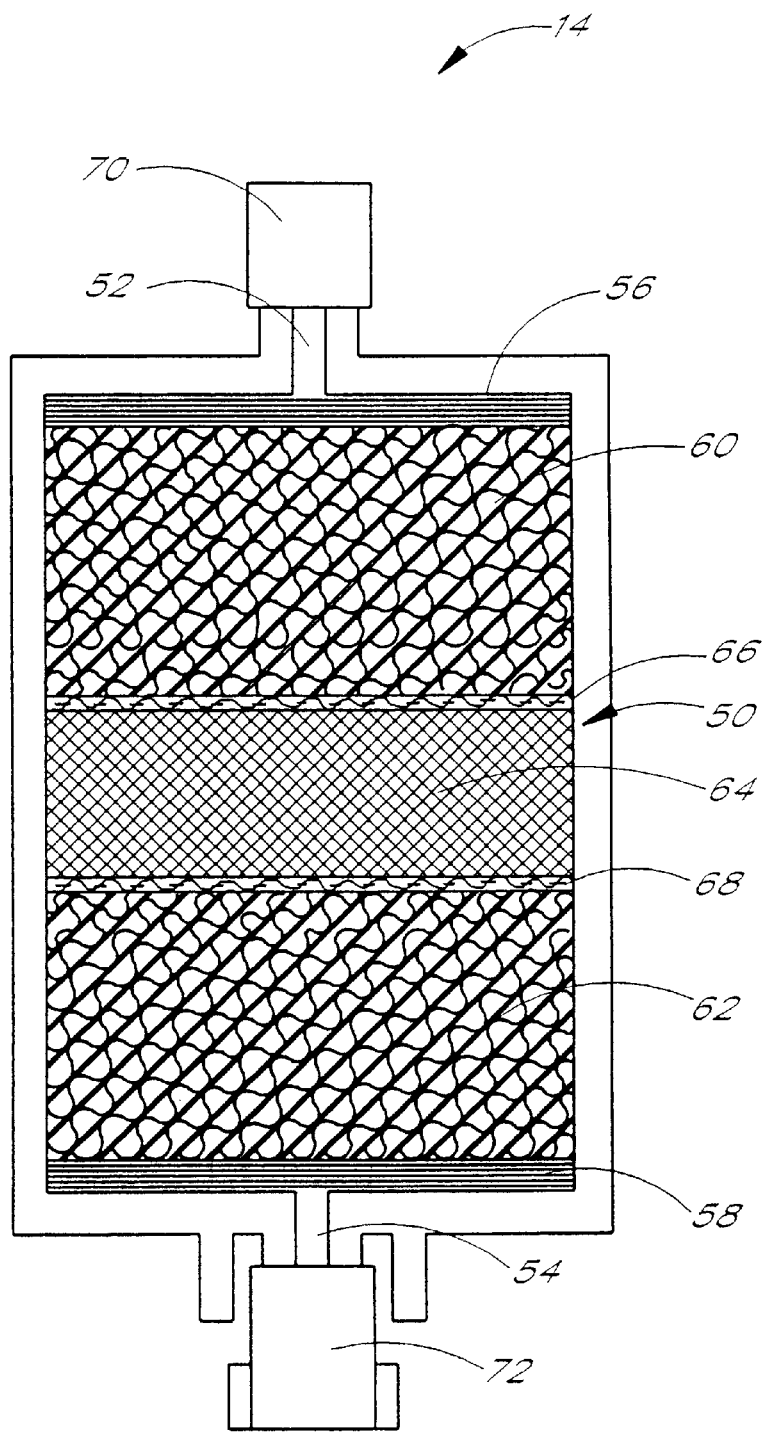
FIG. 4 shows the reagent cartridge of FIG. 3 after partial dissolution of the reagents housed therein.
Figure 5:
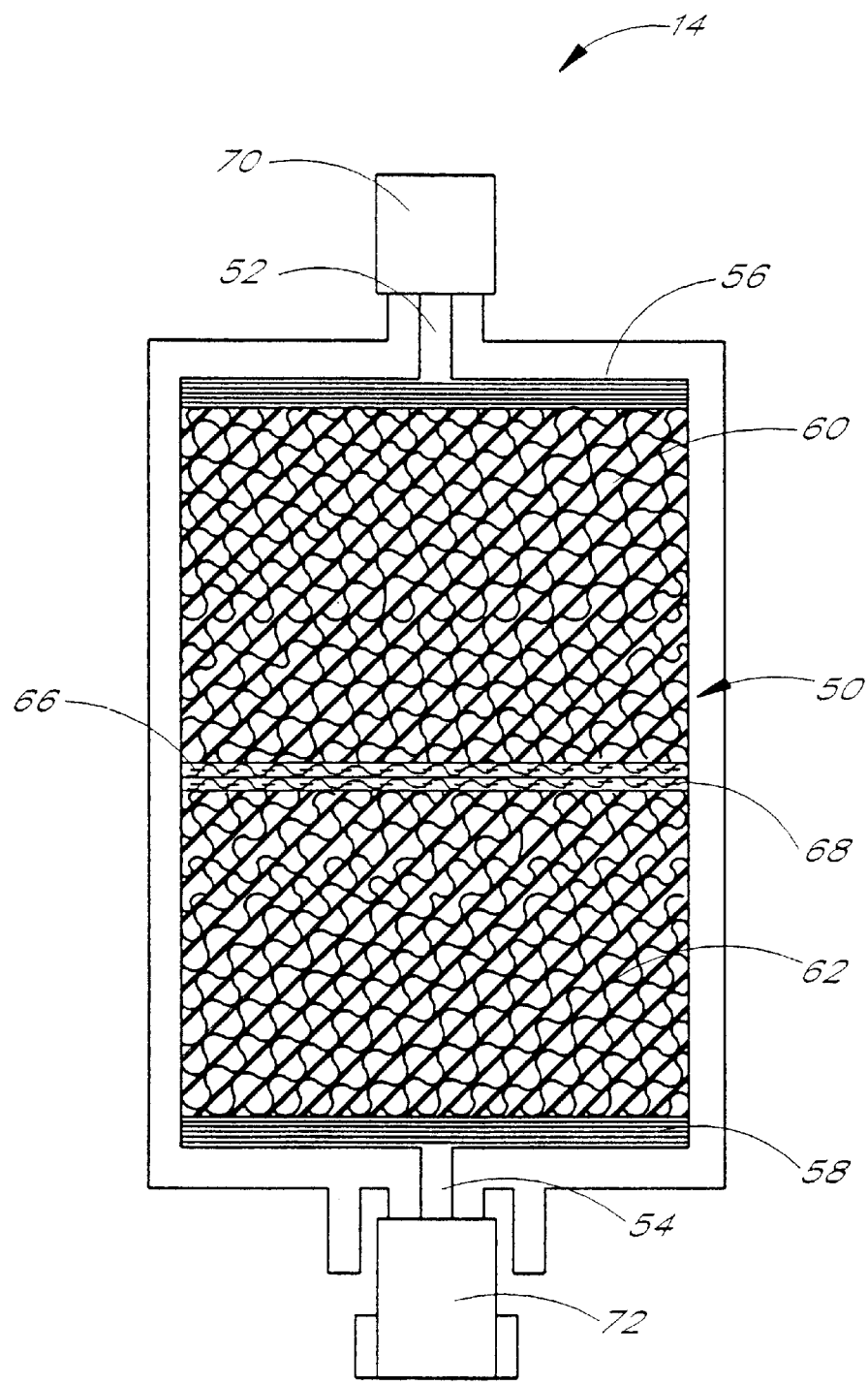
FIG. 5 shows the reagent cartridge of FIG. 3 after complete dissolution of the reagents housed therein.

FIGS. 3–5 illustrate a single-bed reagent cartridge 14, constructed in accordance with a first embodiment. The figures illustrate various stages of dissolution, as will be better understood from the methods of operation discussed hereinbelow.

FIG. 3 shows a filly charged reagent cartridge 14, in accordance with the first embodiment. The cartridge 14 comprises rigid walled housing 50 with an inlet port 52 at an upstream end, and an outlet port 54 at a downstream end. Within the housing, a number of porous elements define a fluid flow path between the inlet port 52 and the outlet port 54.

The housing 50 is preferably transparent or translucent, advantageously enabling the user to observe the operation of the device and complete dissolution of reagents prior to use of a produced solution, as will be apparent from the discussion of the method of operation, discussed hereinbelow. Examples of translucent and transparent polymers are polypropylene, polycarbonate and many other well-known materials.

Within the housing 50, immediately downstream of the inlet port 52, is an inlet frit 56, which serves as a safety filter to contain any reagent which escapes the restraints described below. An outlet frit 58 serves a similar function immediately upstream of the outlet 54. Desirably, the inlet frit 56 and the outlet frit 58 comprise porous elements having a porosity smaller than the smallest particle of the reagents housed within the cartridge 14. The frits 56, 58 thus serve as filters to ensure that no reagent escapes the cartridge prior to dissolution, as will be described below. An exemplary frit is a multilayered polypropylene laminate, having a porosity between about 1 $\mu$m and 100 $\mu$m, more preferably between about 10 $\mu$m to 50 $\mu$m. Further details on the preferred material are given below, with respect to the reagent restraints.

Downstream of the inlet frit 56 is an upstream reagent compression component 60. Similarly, upstream of the outlet frit 58 is a downstream reagent compression component 62. The compression components 60, 62 preferably comprise materials which have sponge-like elasticity and, as a result of compression, exert axial pressure while trying to return to its original, expanded form. The compression components 60, 62 preferably comprise compressible, porous, open cell polymer or foam, desirably more porous than the frits, to avoid generation of back pressure. An exemplary material for the compression components is a polyurethane foam. Desirably, the compression components 60, 62 and surrounding housing 50 are arranged such that the compression components 60, 62 exert a compressive force on the reagent bed regardless of the size of the reagent bed. In other words, the compression components 60 and 62 would, if left uncompressed, together occupy a greater volume than that defined by the housing 50. Desirably, the pressure exerted is between about 50 psi and 500 psi, more preferably between about 100 psi and 300 psi.

It will be understood that, in other arrangements, metal or polymer coiled springs and porous plates can serve the same function. Such alternative compression components are disclosed, for example, with respect to FIGS. 12–15; Col. 9, lines 8–53 of U.S. Pat. No. 5,725,777, the disclosure of which is incorporated herein by reference. It will also be understood, in view of the discussion below, that a single compression component can serve the function of the illustrated two compression components. Two components exerting pressure on either side of a reagent bed 64 (described below), however, has been found particularly advantageous in operation.

A single reagent bed 64 is situated between the compression components 60, 62. The reagent bed 64 is desirably sandwiched between an upstream reagent restraint 66 and a downstream reagent restraint 68. The upstream reagent restraint 66 is thus positioned between the reagent bed 64 and the upstream compression component 60, while the downstream reagent restraint 68 is positioned between the reagent bed 64 and the downstream compression component 62.

The restraints 66, 68 desirably prevent the passage of reagent particles in their dry formulation. The porosity of the restraints is therefore selected to be less than the size of the smallest particles within the reagent bed, depending upon the particular reagent formulations and physical particle size desired. Desirably, the pores are large enough to avoid excessive pressure drop across the restraints. Preferably, the restraint porosity in the range between about 1 $\mu$m and 100 $\mu$m, more preferably between about 10 $\mu$m to 50 $\mu$m. An exemplary restraint, suitable for the illustrated peritoneal dialysis application, comprises the same material as the frits 56, 58, and consists of a non-woven polymer, particularly polypropylene with a porosity of about 20 microns. Another exemplary restraint comprises sintered polyethylene with a porosity of about 30 microns.

Additionally, the restraints 66, 68 are sized and shaped to extend completely across the housing 50, forming an effective seal against reagent particulates escaping around the restraints 66, 68.

In the illustrated embodiment, the reagent bed 64 comprises a complete formulation of dry or lyophilized reagents required to produce a peritoneal dialysis solution. In the illustrated single-bed embodiment, the reagent bed 65 is a mixture of compatible reagents, such as will not exhibit spontaneous chemical reaction from prolonged contact in their dry form. Accordingly, a buffering agent such as an acetate or lactate, and particularly sodium lactate, is employed in place of a bicarbonate. Further reagents include electrolytes, such as sodium chloride, magnesium chloride, potassium chloride and calcium chloride; a sugar, preferably dextrose; and an acid, particularly citric acid. Advantageously, the acid component of the reagent bed 65 can be lower than conventional solutions, since storage in dry form alleviates the tendency for dextrose caramelization.

The illustrated housing 50 holds reagents sufficient to produce 2 liters of a typical peritoneal dialysate solution. Accordingly, the reagent bed 64 holds the following reagents:

TABLE I

| Dry Reagent Constituents | Mass | Dry Volume |
| --- | --- | --- |
| Calcium chloride | 514 mg | Negligible |
| Magnesium chloride | 101.6 mg | Negligible |
| Sodium lactate | 8.96 g | 24 mL |
| Sodium chloride | 10.76 g | 22 mL |
| Dextrose | 50 g | 70 mL |
| Total | 70 g | 101 mL |

The dry volume of the above-listed reagents, which can produce 2 L of 2.5% dextrose peritoneal dialysate, is thus about 100 mL. The housing 50 for such a formulation need only be about 125% to 500% of the dry reagent volume, more preferably about 150% to 200%, depending upon the selected compression components 60, 62. The illustrated housing 50 is about 2" in diameter and about 3" in height, thus occupying about 175 mL. The cartridge 14 thus represents a much smaller and more stable form of dialysate for storage and transport, compared to 2 L of prepared solution. If a smaller or larger volume of solution is desired, the skilled artisan can readily determine the proportionate weight and volume of dry reagents required in the reagent bed 64, such as for producing 1 L, 3 L, 6 L, 10 L, etc. Similarly, the skilled artisan can readily determine the proportions of reagents desirable for 1.5% dextrose dialysate, 4% dextrose dialysate, etc.

The housing inlet port 52 and outlet port 54 are covered by an inlet port cover 70 and an outlet port cover 72, respectively. The port covers 70, 72 advantageously seal out moisture and prevent destabilization of the dry reagents housed within during transport and storage. As with the water purification pack, the inlet port 52 and outlet port 54 can be configured with threaded or Luer-type connection fittings. In the illustrated embodiment, the inlet port 52 is configured to mate with the outlet 24 of the water purification pack 12 (FIG. 2), while the outlet port 54 is configured to mate with the downstream tube 18 (see FIG. 1).

Double-Bed Reagent Cartridge

Figure 6:
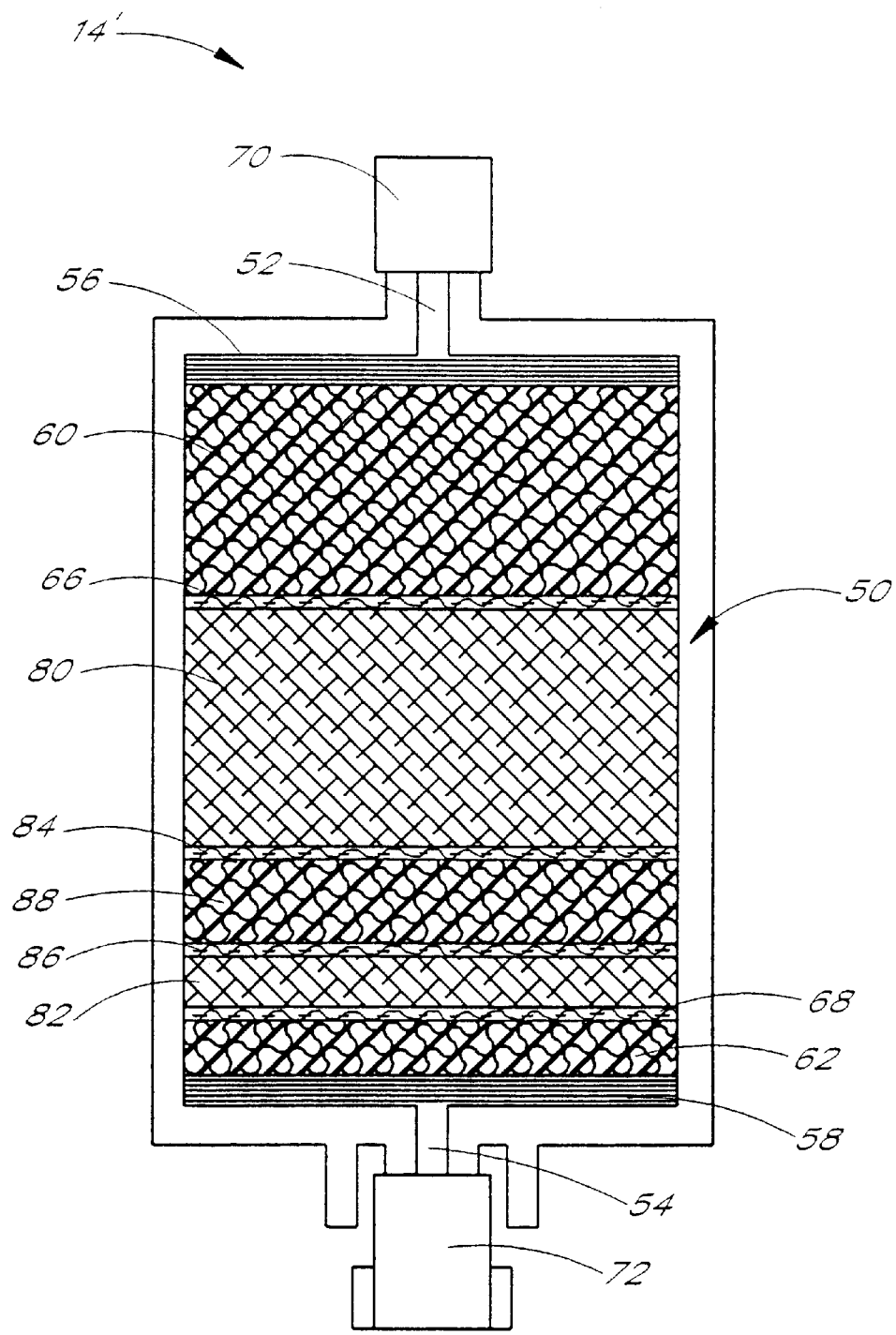
FIG. 6 is a schematic side sectional view of a reagent cartridge for housing reagents of peritoneal dialysate, constructed in accordance with another preferred embodiment of the present invention.
Figure 7:
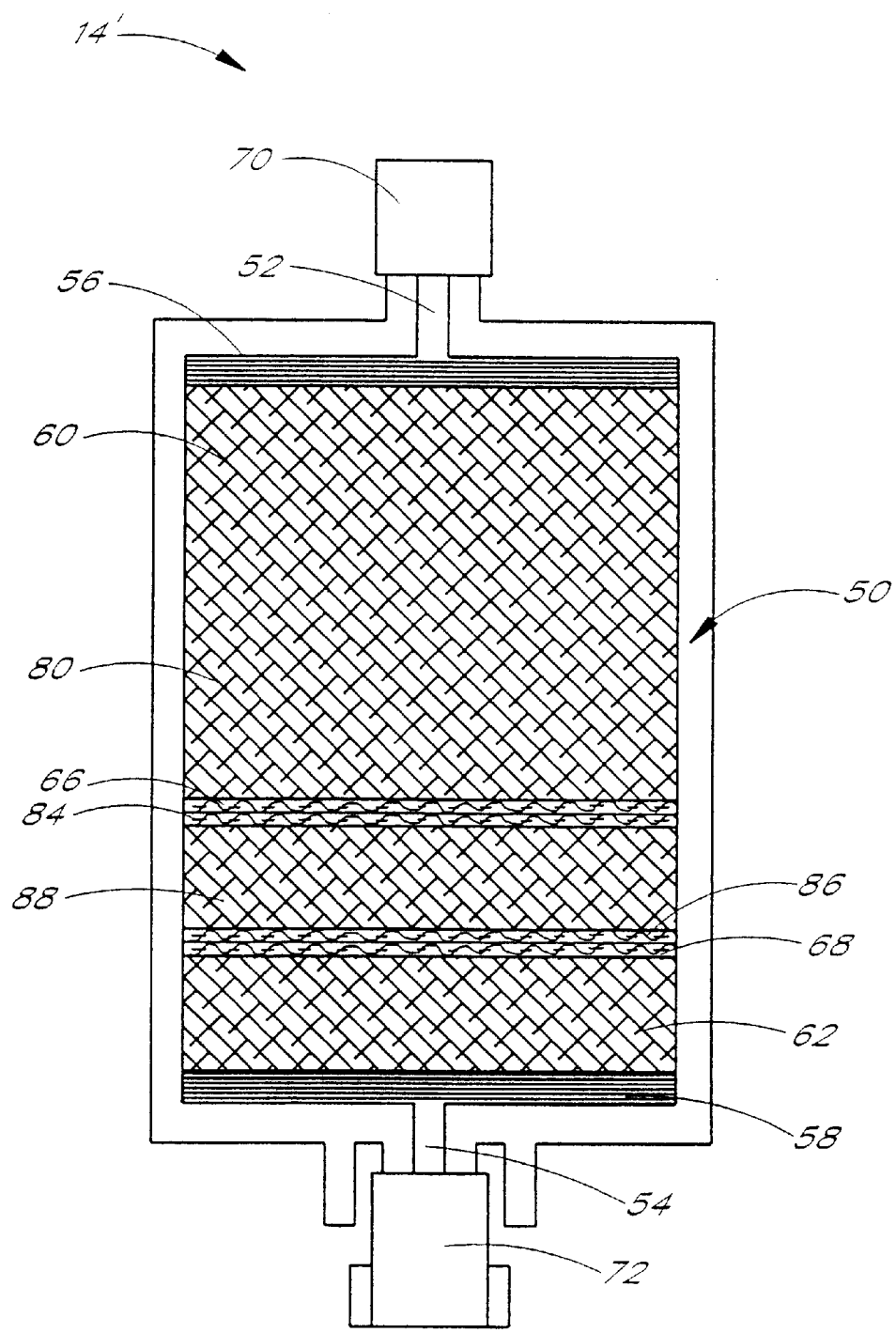
FIG. 7 shows the reagent cartridge of FIG. 6 after complete dissolution of the reagents housed therein.

FIGS. 6 and 7 illustrate a double-bed reagent cartridge 14', constructed in accordance with a second embodiment FIGS. 6 and 7 illustrate the cartridge 14' in fully charged and fully depleted conditions, respectively, as will be better understood from the methods of operation discussed hereinbelow.

With reference initially to FIG. 6, the housing 50 of the double-bed reagent cartridge 14' is preferably similar to that of the first embodiment, such that like reference numerals are used to refer to like parts. Thus, the housing 50 defines an inlet port 52 and outlet port 54, and contains porous elements between the inlet port 52 and outlet port 54, such as to define a fluid flow path through the housing 50. Specifically, the housing 50 contains an upstream frit 56, upstream compression component 60, upstream reagent restraint 66, downstream reagent restraint 68, downstream compression component 62 and downstream frit 58. Each of these elements can be as described with respect to the previous embodiment.

Unlike the single-bed cartridge 14 of FIGS. 3–5, however, multiple reagent beds are confined between the upstream restraint 66 and downstream restraint 68. In particular, a primary reagent bed 80 and a secondary reagent bed 82 are shown in the illustrated embodiment, separated by at least one restraint. In the illustrated embodiment, the reagent beds 80 and 82 are separated by a first intermediate restraint 84 and second intermediate restraint 86, as well as an intermediate compression component 88 between the intermediate restraints 84 and 86.

Accordingly, the primary reagent bed 80 is confined between upstream restraint 66 and the first intermediate restraint 84, while the secondary reagent bed 84 is similarly confined between the second intermediate restraint 86 and the downstream restraint 68. The intermediate reagent bed restraints 84, 86 desirably serve to contain the reagents within the beds 80, 82 in their dry form, while still being porous enough to allow diluent, along with any dissolved reagents, to pass through. Accordingly, the intermediate reagent restraints 84, 86 can have the same structure as the frits 56, 58 and upstream and downstream reagent restraints 66, 68, as described above with respect to the single-bed embodiment. Similarly, the intermediate compression component 88 can have the same structure as the upstream and downstream compression components 60, 62.

Each of the intermediate compression component 88 and the intermediate reagent restraints 84, 86 are interposed between and separate the primary reagent bed 80 from the second reagent bed 82. Due to the selected porosity of the elements, particularly the intermediate restraints 84, 86, constituents of the two reagent beds 80, 82 therefore do not interact with one another in their dry states.

The illustrated double-bed embodiment therefore enables separate storage of different reagents within the same housing 50. A complete formulation of the dry reagents required to produce a peritoneal dialysis solution may contain reagents that react undesirably when exposed to one other for prolonged periods of time, in either dry or liquid forms, as noted in the Background section. For example, bicarbonates are preferred, physiologically compatible buffering agents for peritoneal dialysis, but tend to be very reactive with typical salts in the dialysate formulation, such as calcium chloride or magnesium chloride. The reactions form insoluble calcium carbonate or magnesium carbonate, and also liberate $CO_2$. Because of the potential reactivity of incompatible reagents, it is preferable to separately store these reagents within the device housing 50.

Separate storage is accomplished by separating reagents into compatible groupings, which are then placed in separate compartments within the housing. The compartments are represented, in the illustrated embodiment, by the primary reagent bed 80 and the secondary reagent bed 82. The potentially reactive reagents are thereby constrained from movement through the housing, when maintained in their dry form, by reagent bed restraints 66, 84, 86, 68 at the upstream and downstream ends of each of the reagent beds 80, 82. As noted above, the reagent bed restraints 66, 84, 86, 68 have fine enough porosity to prevent the passage of reagent particles in their dry form.

In the illustrated embodiment, the primary reagent bed 80 is a reagent mixture, preferably comprising: electrolytes, particularly sodium chloride, potassium chloride, calcium chloride and magnesium chloride; a sugar, particularly dextrose. In other arrangements, the primary reagent bed 80 can also comprise a buffer.

The secondary reagent bed 82 can contain at least one component which is unstable in the presence of at least one component in the primary reagent bed 80. Advantageously, the secondary reagent bed 82 contains a bicarbonate, such as sodium bicarbonate. Because the bicarbonate is separated from calcium chloride and magnesium chloride, the reagents do not react to form insoluble precipitates.

The skilled artisan will readily appreciate that, in other arrangements, the primary reagent bed 80 can contain the bicarbonate if the secondary bed 82 contains calcium chloride and/or magnesium chloride. In still other alternatives, other incompatible reagents for medical solutions can be similarly separated into reagent beds within the same housing. Moreover, three or more reagent beds can be utilized to separate multiple incompatible reagents.

The illustrated housing 50 holds reagents sufficient to produce 2 liters of a typical peritoneal dialysate solution. Accordingly, the reagent beds 80, 82 hold the following reagents:

TABLE II

|  | Mass | Dry Volume |
|---|---|---|
| Primary Reagent Bed |  |  |
| Calcium chloride | 514 mg | negligible |
| Magnesium chloride | 101.6 mg | negligible |
| Sodium chloride | 10.76 g | 22 mL |
| Dextrose | 50 g | 70 mL |
| Subtotal | 61 | 92 mL |
| Secondary Reagent Bed |  |  |
| Sodium bicarbonate | 6.64 g | 61 mL |
| Total | 68 g | 98 mL |

The dry volume of the above-listed reagents, which can produce 2 L of 2.5% dextrose peritoneal dialysate, is thus about 98 mL. As with the previously described single-bed embodiment, the total volume of the cartridge 14' is preferably between about 125% and 500%, and more preferably 150% and 200%, of the dry reagent volume. As also noted above, the skilled artisan can readily determine the proportionate weights and volumes of dry reagents required for forming other peritoneal dialysate solutions, such as 1.5% dextrose dialysate, 4% dextrose dialysate, etc.

Notably, the double-bed cartridge utilizes bicarbonate as the buffer, and omits the need for physiologically damaging acid by enabling production of a physiologic solution.

Method of Operation

In operation, purified diluent is provided to a reagent cartridge 14 or 14', which is fully charged with an appropriate amount of dry reagent, as set forth above. Diluent may comprise filtered and de-ionized water that is independently provided at the point of administration. It will be understood that other physiologically compatible diluents can also be employed. In the preferred embodiment, however, available water (e.g., municipal tap water) is provided to the system 10 of FIG. 1, such that the purified diluent is produced on site and need not be produced remotely and transported, significantly reducing the cost of transportation.

Accordingly, with reference to FIG. 2, diluent in the form of available potable water is first provided to water purification pack 12 of FIG. 2. Pressures commonly found in municipal water systems is sufficient to feed the water through the purification pack 12. Alternatively, a hand pump or large syringe can be supplied with a measured volume of water, and water hand pumped therefrom into the purification pack 12.

The diluent enters the inlet 22 and passes through depth filter 26, where particulates larger than about 1 micron are filtered out. Filtered diluent continues downward through granular carbon bed 28, where residual organics such as endotoxins and additives such as chlorine, chloramine and trihalomethanes are absorbed. After being additionally filtered by carbon bed restraint 30, the partially purified diluent passes into deionization resin bed 32. Dissociated ions and other charged particulates in solution bind to the resins. Endotoxins which have escaped the upstream components are also retained in the resin bed 32. After passing through the resin bed restraint 34, which retains the contents of the resin bed 34, the diluent is further filtered through the terminal filter element 36. This filter 36 has a very fine porosity (e.g., about 0.2 micron or finer), and includes chemical treatment with a quaternary amine exchanger for binding residual endotoxins.

The multiple filtration and chemical binding components of the water purification pack 12 thus ensure removal of particulate, ionic and organic contaminants from the diluent as it passes through the pack 12. Endotoxins, including organic matter such as cell walls from dead bacteria, can be particularly toxic. Highly purified diluent, sufficient to comply with the water quality standards of the U.S. pharmacopoeia for "sterile water for injection," exits the outlet 24. With reference to FIG. 1 again, purified diluent then passes from the water purification pack 12 to the reagent cartridge 14.

FIGS. 3–5 illustrate dissolution of dry reagent 64 as diluent passes through the single-bed reagent cartridge 14 of the first embodiment. While illustrated cross-sectionally, it will be understood that the preferred transparent or translucent housing 50 enables the user to similarly observe dissolution of the reagent bed 64 as solvent or diluent passes therethrough. Additionally, the user can observe whether insoluble precipitates are present within the reagent bed, prior to employing the cartridge 14. Advantageously, gravitational force is sufficient to draw the water through the cartridge 14.

Referring initially to FIG. 3, purified diluent enters the cartridge 14 through the inlet port 52. Preferably, purified diluent is fed directly from the water purification pack 12. "Directly," as used herein, does not preclude use of intermediate tubing, etc, but rather refers to the fact that water is purified on site immediately prior to solution formation, rather remotely produced and shipped. It will also be understood, however, that the illustrated reagent cartridge will have utility with other sources of sterile diluent.

The diluent passes through the porous inlet frit 56 and the upstream compression component 60. In the illustrated embodiment, the compression component 60 is a porous, open-celled foam, which readily allows diluent to pass therethrough. The diluent then passes through the upstream reagent restraint 66 to reach the dry reagent bed 64. In addition to retaining the dry reagents in the bed 64, the frit 56 and restraint 66 facilitate an even distribution of water flow across the sectional area of the housing 50.

As the solution passes through interstitial spaces in the bed 64, the dry reagents are erroded, preferably dissolved, and carried by the diluent through the downstream reagent restraint 68, the downstream compression component 44 and the outlet frit 58, exiting through outlet 24. The solution passes through the tube 18 into the collection reservoir 16 (see FIG. 1) or directly into the peritoneal cavity of a patient.

Referring to FIG. 4, as the reagents are dissolved, the volume of the reagent bed 64 is reduced, as can be seen from a comparison of FIG. 4 with FIG. 3. The compression components 60, 62 apply continuous compressive force on either side of the reagent bed 64. As dry reagent is dissolved, the compressive force packs the reagents close together. Such continuous packing prevents expansion of interstitial spaces as the reagent particles are dissolved. Without the compressive force, the interstitial spaces between the reagent particles tend to expand into larger channels within the reagent bed 64. These channels would serve as diluent flow paths, which would permit a large volume of diluent to flow through the bed 64 with minimal further dissolution. Significant portions of the bed would be by-passed by these channels, and dissolution would be slow and inefficient. Applying continuous compression to the beds minimizes this problem by continuously forcing the reagent particles together as the bed dissolves, ensuring continuous, even exposure of the diluent to the reagents of the bed 64.

Though two compression components 60, 62 are preferred, thus compressing the reagent bed 64 from two sides, it will be understood that a single compression component can also serve to keep the regent beds 64 compacted. Moreover, though illustrated in an axial arrangement, such that diluent flows through the compression components 60, 62, it will be understood that the compression components can exert a radial force in other arrangements.

The compressive force of the preferred compression components 60, 62, exerted evenly across the housing 50, additionally aids in maintaining the planar configuration of the reagent restraints 66, 68 on either side of the reagent bed 64, even as the compression components 60, 62 move the restraints inwardly. The restraints 66, 68 thus continue to form an effective seal against the housing sidewalls, preventing dry reagent particulates from escaping the bed 64 until dissolved.

With reference to FIG. 5, dissolution continues until the reagent bed is depleted and the restraints 66, 68 contact one another. Diluent can continue to flow through the housing 50 into the reservoir 16 (FIG. 1) until the appropriate concentration of peritoneal dialysate solution is formed. For example, in the illustrated embodiment, 2 liters of diluent should be mixed with the contents of the reagent bed 64. Accordingly, 2 liters of diluent are passed through the housing 50. The contents are typically fully dissolved by the time about 1.5 liters has passed through the housing, but diluent can continue to flow until the appropriate final concentration is reached in the reservoir. Alternatively, a concentrate can be first formed and independently diluted.

Advantageously, the illustrated apparatus and method can form peritoneal dialysis solution simply by passing water through the cartridge 50, without complex or time consuming mixing equipment. The solution can thus be formed on-site, immediately prior to delivery to the peritoneal cavity, such that the dialysate need not be shipped or stored in solution form. Accordingly, a low acid level is possible without undue risk of dextrose carmelization. Conventionally, a pre-formed dialysis solution formed has a pH between about 4.0 and 6.5, and the exemplary reagent mix of Table I produces a conventional solution with pH of about 5.2. Solution produced from the illustrated single-bed cartridge of FIGS. 3–4, however, can have lower acidity, since dextrose does not sit in solution for extended periods of time. Accordingly the pH level is preferably between about 6.0 and 7.5, more preferably about 7.0.

Referring to FIGS. 6 and 7, the double-bed reagent cartridge 14' operates in similar fashion. Purified diluent is fed to the housing inlet 52, and passes through the inlet frit 56, the upstream compression component 60, the upstream restraint 66, and into the primary reagent bed 80. Dissolution of reagents in the primary bed 80 forms a solution which passes on through the first intermediate restraint 84, the intermediate compression component 88 and the second intermediate restraint 86. Reagents in the secondary bed 82 then also dissolve into the diluent, and the enriched solution continues on through the downstream reagent restraint 68, the downstream compression component 62 and the outlet frit 58. A complete solution thus exits the outlet port 54.

As in the previous embodiment, the regent beds 80, 82 are continually compressed as the reagents dissolve. Use of three compression components 60, 88, 62 has been found to improve dissolution by compressing each bed 80, 82 from two sides. The skilled artisan will understand, however, that two compression components, in the positions of the upstream and downstream third components, can adequately serve to keep the reagent beds compressed enough to aid the rate of dissolution, particularly if provided with a high degree of elasticity. Similarly, a single intermediate compression component, in the position of the illustrated intermediate compression component 88, can accomplish this function, while advantageously also separating the incompatible reagent beds. Additionally, the compression component need not be axially aligned with the reagent beds, but could instead surround or be surrounded by the reagent beds, in which case the compression components would preferably be outside the diluent flow path.

Advantageously, the illustrated embodiments provide stable, dry forms of peritoneal dialysis solutions. Storage and transport of the reagent cartridges of the illustrated embodiments represents considerable cost savings over storage and transport of prepared peritoneal dialysate solutions. Dry or lyophilized reagents are moreover more stable than solution, and therefore less harmful to the patient.

While the storage and transport of dry reagents is generally recognized as advantageous, practical application has been difficult. The described embodiments not only provide transport and storage, but additionally provide integrated mechanisms to ensure complete dissolution of the dry reagents. Continuous compression of the reagent bed(s) during dissolution, combined with the transparent windows allowing real time viewing of the dissolution, ensure rapid, complete and verifiable dissolution of the reagents. Thus, the preferred embodiments can be utilized on site, even in the home, without requiring complex mixing and/or analytical tools.

Moreover, the illustrated embodiments facilitate a wider practicable range of reagents. For example, physiologically compatible bicarbonate can be employed along with calcium and magnesium. Separate storage and solution preparation only immediately prior to administration enables this combination. High dextrose solutions, as appropriate for peritoneal dialysis, can be employed without acidic buffers, such that physiologically compatible pH levels can be practically obtained, preferably between about 4.0 and 7.5, and more preferably between about 6.0 and 7.5. The reagents listed in Table II produce a solution with a pH of about 7.0.

Additionally, the preferred arrangement includes a water purification pack 12, obviating transport of sterile diluent. Thus, the bulk of peritoneal dialysis solution can be provided through tap water at the site of peritoneal dialysis administration. Potable water is purified through the water purification pack, and thus purified water fed through a reagent cartridge. Simply by gravitational action, water flow through the cartridge results in complete dissolution of dry reagents and produces a complete solution suitable for peritoneal dialysis.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the dependent claims.

What is claimed is:

1. An apparatus for producing a peritoneal dialysis solution comprising:
    a housing defining a fluid flow path therethrough; and
    at least one reagent bed within the housing along the fluid flow path, wherein the at least one reagent bed comprises dry reagents in proportions suitable for peritoneal dialysis, wherein the reagent bed contains different reagents.

2. The apparatus of claim 1, further comprising a compression component adjacent the at least one reagent bed.

3. The apparatus of claim 2, wherein the compression component comprises a compressible foam member.

4. The apparatus of claim 2, wherein the compression component is positioned within the fluid flow path, and comprises an open cell compressible foam member.

5. The apparatus of claim 2, wherein the compression component comprises a coiled spring.

6. The apparatus of claim 2, wherein the at least one reagent bed is compressed between an upstream compression component and a downstream compression component.

7. The apparatus of claim 6, wherein the at least one reagent bed is confined between an upstream reagent restraint, positioned between the upstream compression component and the at least one reagent bed, and a downstream reagent restraint, positioned between the downstream compression component and the at least one reagent bed.

8. The apparatus of claim 6, wherein the at least one reagent bed includes dry forms of electrolyte salts, dextrose, and a buffer.

9. The apparatus of claim 6, wherein the at least one reagent bed comprises a first reagent bed and a second reagent bed.

10. The apparatus of claim 9, wherein the first reagent bed is downstream of the second reagent bed.

11. A system for producing a peritoneal dialysis solution, comprising:
    a reagent cartridge housing at least one dry reagent bed and at least one compression component exerting continual pressure on the at least one dry reagent bed; and
    a water purification pack configured to connect upstream of the reagent cartridge, the water purification pack housing filters, activated carbon and ion exchange resins such as to convert potable water to injectable quality water.

12. The system of claim 11, wherein the cartridge includes dry reagents sufficient to produce a complete formulation of peritoneal dialysis solution.

13. The system of claim 12, wherein the at least one reagent bed includes dry reagents suitable for forming 2 liters of peritoneal dialysis solution.

14. The system of claim 12, wherein the reagent bed includes dry reagents suitable for forming 2.5% dextrose peritoneal dialysis solution.

15. The apparatus of claim 11, wherein the at least one reagent bed comprises a first reagent bed and a second reagent bed.

16. The apparatus of claim 15, wherein the first reagent bed is downstream of the second reagent bed.

17. A system for producing a peritoneal dialysis solution, comprising:
- a reagent cartridge housing a first reagent bed and a second reagent bed and at least one compression component exerting continual pressure on the reagent beds, wherein the first reagent bed and the second reagent bed contain different reagents; and
- a water purification pack configured to connect upstream of the reagent cartridge, the water purification pack housing filters, activated carbon and ion exchange resins such as to convert potable water to injectable quality water.

18. The system of claim 17, wherein the cartridge includes dry reagents sufficient to produce a complete formulation of peritoneal dialysis solution.

19. The system of claim 18, wherein the first reagent bed and the second reagent bed comprise dry reagents suitable for forming 2 liters of peritoneal dialysis solution.

20. The system of claim 18, wherein the first reagent bed and the second reagent bed comprise dry reagents suitable for forming 2.5% dextrose peritoneal dialysis solution.

* * * * *